US010010362B2

(12) United States Patent
Vogt et al.

(10) Patent No.: US 10,010,362 B2
(45) Date of Patent: Jul. 3, 2018

(54) DEVICE FOR STORING AND MIXING BONE CEMENT

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 544 days.

(21) Appl. No.: 14/611,419

(22) Filed: Feb. 2, 2015

(65) Prior Publication Data

US 2015/0216577 A1 Aug. 6, 2015

(30) Foreign Application Priority Data

Feb. 3, 2014 (DE) .................. 10 2014 101 305

(51) Int. Cl.
*A61B 17/88* (2006.01)
*B01F 15/02* (2006.01)
(Continued)

(52) U.S. Cl.
CPC ...... *A61B 17/8833* (2013.01); *B01F 11/0054* (2013.01); *B01F 11/0082* (2013.01);
(Continued)

(58) Field of Classification Search
CPC .......... B01F 2215/0029; B01F 15/0205; B01F 15/0206; B01F 15/0212; B01F 15/0213;
(Continued)

(56) References Cited

U.S. PATENT DOCUMENTS 3,144,966 A     8/1964   Cook
3,370,754 A *   2/1968   Schumann ........... A61C 9/0026
                                                                222/132
(Continued)

FOREIGN PATENT DOCUMENTS

AU     2014256326 A1    7/2015
CA       2708462 A1   12/2010
(Continued)

OTHER PUBLICATIONS

Chinese Office Action for corresponding Chinese Application No. 2015100503170 dated Sep. 5, 2016.
(Continued)

*Primary Examiner* — David C Mellon
(74) *Attorney, Agent, or Firm* — Norris McLaughlin & Marcus P.A.

(57) ABSTRACT

A device and/or method stores, mixes, and applies polymethylmethacrylate bone cement, wherein the device and/or method comprising a first container for a first pasty component, a dispensing plunger that is arranged such that it can be shifted in the first container and serves for extruding the content of the first container through a dispensing tube opposite from the dispensing plunger. The dispensing tube can be rotated and shifted in longitudinal direction through a feed-through in a side of the first container opposite from the dispensing plunger. A mixing facility is arranged in the first container, is secured to the dispensing tube, and is movable in the first container by moving the dispensing tube. At least one second container for at least one second component is arranged on the first container, whereby the internal space of the at least one second container is closed with respect to the internal space of the first container by means of a closure, which is openable. The at least one second container is limited, on the side opposite from the closure, by a dosing plunger, and whereby at least one
(Continued)

limiting surface of the first container is formed by a mobile volume compensation element.

22 Claims, 8 Drawing Sheets

(51) Int. Cl.
*B01F 13/00* (2006.01)
*B01F 11/00* (2006.01)

(52) U.S. Cl.
CPC ...... *B01F 13/0023* (2013.01); *B01F 15/0215* (2013.01); *B01F 15/0225* (2013.01); *B01F 15/0278* (2013.01); *A61B 2017/8838* (2013.01); *B01F 2215/0029* (2013.01)

(58) Field of Classification Search
CPC .............. B01F 15/0215; B01F 15/0225; B01F 15/0237; B01F 15/0238; B01F 15/0258; B01F 15/0259; B01F 15/0278; B01F 15/0279; B01F 2015/0273; B01F 13/06; B01F 13/002; B01F 13/0023; B01F 13/0027
USPC .... 366/139, 189, 190, 182.2, 255, 256, 260, 366/275, 267, 269, 268
See application file for complete search history.

(56) References Cited

U.S. PATENT DOCUMENTS

| | | | |
|---|---|---|---|
| 3,735,900 A | 5/1973 | Gores | |
| 4,208,133 A | 6/1980 | Korte-Jungermann | |
| 4,676,406 A | 6/1987 | Frischmann et al. | |
| 5,017,349 A | 5/1991 | Davis et al. | |
| 6,017,349 A | 1/2000 | Heller et al. | |
| 7,079,936 B2* | 7/2006 | Honda | F02D 35/023 701/102 |
| 2005/0128868 A1* | 6/2005 | Vries | A61B 17/8825 366/139 |
| 2006/0227653 A1* | 10/2006 | Keller | A61B 17/00491 366/139 |
| 2009/0105144 A1 | 4/2009 | Vogt et al. | |
| 2009/0105366 A1 | 4/2009 | Vogt et al. | |
| 2010/0329074 A1 | 12/2010 | Vogt et al. | |
| 2013/0125786 A1 | 5/2013 | Vogt | |
| 2013/0135957 A1 | 5/2013 | Vogt et al. | |
| 2015/0164568 A1 | 6/2015 | Vogt | |

FOREIGN PATENT DOCUMENTS

| | | |
|---|---|---|
| DE | 28 08 230 A1 | 8/1979 |
| DE | 8505393 U1 | 4/1985 |
| DE | 34 21 823 A1 | 5/1985 |
| DE | 3411194 A1 | 10/1985 |
| DE | 3744161 A1 | 7/1989 |
| DE | 10127625 A1 | 1/2003 |
| DE | 102007052116 A1 | 4/2009 |
| DE | 102007050762 B3 | 5/2009 |
| DE | 102008030312 A1 | 1/2010 |
| EP | 0 882 436 A1 | 12/1998 |
| EP | 1 264 640 A2 | 12/2002 |
| EP | 2596812 A1 | 5/2013 |
| EP | 2 883 603 A1 | 6/2015 |
| JP | H114836 A | 1/1999 |
| JP | 2011005255 A | 1/2011 |
| WO | 89/05763 | 6/1989 |

OTHER PUBLICATIONS

Japanese Office Action for corresponding Japanese Application No. 2015-014289 dated Jun. 14, 2016.

* cited by examiner

DEVICE FOR STORING AND MIXING BONE CEMENT

The invention relates to a device for storing, mixing, and applying polymethylmethacrylate bone cement, and to a method for producing a polymethylmethacrylate bone cement using said device.

Accordingly, the subject matter of the invention is a device for storing and mixing polymethylmethacrylate bone cement that consists, during storage and prior to mixing, of a liquid or pasty first component A and separate powdery or pasty second component B, as well as a method for mixing, and applying if applicable, the two components and, if desired, an additional pharmaceutical agent.

Polymethylmethacrylate bone cements (PMMA bone cements) have been in use in medicine for decades for permanent mechanical fixation of total joint endoprostheses. These are based on powder-liquid systems, whereby it is customary to use methylmethacrylate as monomer. Recently, polymethylmethacrylate bone cements that are based on the use of cement pastes have been proposed as well (DE 10 2007 050 762 B3, DE 10 2008 030 312 A1, DE 10 2007 052 116 A1). These bone cements have two cement pastes stored separately in suitable cartridges. Cartridges of this type are also often referred to as 2-component cartridges (also as 2K-cartridges). These each contain components of a redox initiator system, aside from at least one monomer and suitable polymers.

Methylmethacrylate is the monomer used most commonly in polymethylmethacrylate bone cements. Redox initiator systems usually consist of peroxides, accelerators and, if applicable, suitable reducing agents. Radicals are formed only if all components of the redox initiator systems act in concert. For this reason, the components of the redox initiator system are arranged appropriately in the separate cement pastes such that these cannot trigger a radical polymerisation. The cement pastes are stable during storage provided their composition is adequate. Only when the two cement pastes are mixed to produce a cement dough, the components of the redox initiator system, previously stored separately in the two pastes, react with each other forming radicals which trigger the radical polymerisation of the at least one monomer. The radical polymerisation then leads to the formation of polymers while consuming the monomer, whereby the cement dough is cured. It is customary to use static mixers for mixing the cement pastes and to attach them for this purpose to the two-component cartridges filled with the cement pastes.

When the two cement pastes are extruded from the cartridges, the two cement pastes are pushed through a static mixer. The processes of extruding and mixing thus proceed concurrently. Mixing the cement pastes in the static mixer requires a high extrusion force since the pressure drop at the mixing elements in the static mixer is very high. It is therefore necessary to use powerful pneumatic or mechanical extrusion devices to dispense and optimally mix the cement pastes. Said pneumatic or mechanical extrusion devices are elaborate from a technical point of view and expensive. A less expensive option are the manually-operated extrusion guns, which are customary with the polymethylmethacrylate bone cements based on powder-liquid systems, which are suitable for said cements, but are not sufficiently powerful for extruding and mixing bone cement pastes through the use of static mixers.

In conventional two-component cartridges, the volume ratio of component A to component B is 1:1, 1:2, and 1:10. The more the volumes of the components to be mixed through the use of static mixers differ, the more difficult it is to generate a homogeneously mixed bone cement paste. For this reason, very many mixing spirals are needed for larger volume ratios. The larger the number of mixing spirals needed, the larger is the pressure drop in the static mixer during the mixing process. One pasty component needs to be present, whereas the second component can be either liquid or powdery or pasty as well. The components and/or pastes need to be pressed through the static mixer by a very large force. Due to the nature of manually-operated extrusion devices, the maximally possible extrusion force is limited.

The SEMKIT® system is time-proven in the adhesives and sealants industry for many years. It involves storing a paste in a storage container. A second liquid component is present in a stirring rod, separated from the paste through a valve that is integrated into the stirring rod. Actuating the valve allows the liquid to flow into the paste which can then be mixed by hand.

Said system is disadvantageous, though, in that the valve system is suitable for viscous media only. The customary monomer of pasty polymethylmethacrylate bone cements, i.e. methylmethacrylate, cannot be separated permanently from the paste by this valve. Moreover, volume fluctuations arising during the axial mixing motion of the stirring rod in non-compressible pastes are compensated for in this system, firstly, in that the cartridges are soft and can change shape and/or expand and, secondly, in that the feed-through for the stirring rod is not absolutely tight such that mixed paste can leak and a small amount of air can also be drawn into the mixed paste. For pasty polymethylmethacrylate bone cements, solid cartridges of a stable shape are required, since the relatively viscous pasty polymethylmethacrylate bone cement dough can be extruded from storage containers and/or cartridges only through very large extrusion forces. Moreover, with bone cements, it is not feasible to use a mixing system, in which inadvertent leakage of small amounts of paste takes place and in which there is the possibility that air is drawn into the paste. This would not only impair the cleanliness in the operating room, but also mechanically weaken the cement dough through the introduction of air since air bubbles in the cured cement act as fissure initiation sites and thus reduce the stability of the cured bone cement. Therefore, the SEMKIT® system cannot be used for pasty polymethylmethacrylate bone cements.

Accordingly, it is the object of the invention to overcome the disadvantages of the prior art. In particular, a simple and inexpensive device for storing and mixing polymethylmethacrylate bone cement is to be developed that can be used to store at least one polymethylmethacrylate bone cement component while excluding air, whereby it shall be feasible, after mixing of the cement components, to dispense the cement dough with customary, inexpensive, manually-operated cementing guns. In this context, the main component of the polymethylmethacrylate bone cement shall be a cement paste and the second component can be pasty or can preferably be present as a powder. The mixing process must not be associated with any inadvertent leakage of cement dough and no air must be drawn into the cement dough due to volume fluctuations during the mixing process. The device shall also be suitable to ensure safe mixing of the two pastes at a volume ratio of the components from 1:10 to 01:30 in order to obtain homogeneous cement dough. It shall be possible to store the two components of the bone cement separately and to combine them safely by actuating a closure device.

Another aim of the present invention is to ensure that, to the extent possible, no residues from opening or cutting a film open, such as with a packaging or a protective film, can remain in the cement dough. The opening, through which the second component is fed into the main component, shall have a reproducible cross-sectional surface area, which, to the extent possible, does not change while the components are being mixed. Moreover, the opening of the dispensing tube towards the container, in which the components are being mixed, shall always have a pre-determined cross-sectional surface area. Said cross-sections shall not be altered if at all possible.

It is another object of the invention to provide for the dispensing tube of the device to be safely patent for the cement dough after the cement components are mixed and the closure is opened, whereby the opening of the dispensing tube must be secured against being blocked by the opened closure while the cement dough is being extruded. Moreover, a method for mixing pasty polymethylmethacrylate bone cements involving the use of the device to be developed is to be provided.

The objects of the invention are met by a device for storing, mixing, and applying polymethylmethacrylate bone cement, comprising a first container for a first pasty component of the bone cement, a dispensing plunger that is arranged such that it can be shifted in the first container and serves for extruding the content of the first container through a dispensing tube opposite from the dispensing plunger, whereby the dispensing tube is arranged such that it can be rotated and shifted in longitudinal direction through a feed-through in a side of the first container opposite from the dispensing plunger, and a mixing facility for mixing the content of the first container, whereby the mixing facility is arranged in the first container and is secured to the dispensing tube such that the mixing facility can be moved in the first container by moving the dispensing tube in order to mix the content of the first container, whereby at least one second container for at least one second component of the bone cement is arranged on the first container, whereby the internal space of the at least one second container is closed with respect to the internal space of the first container by means of a closure, which can be opened, and [whereby] the at least one second container is limited, on the side opposite from the closure, by a dosing plunger, and whereby at least one limiting surface of the first container is formed by a mobile volume compensation element.

According to the invention, the components for the bone cement can be present in the first container and the at least one second container.

Preferably, the first component is free of air. Preferably, the second component is powdery or pasty, particularly preferably it is a self-sterilising paste. Self-sterilising pastes can contain, for example, hydrogen peroxide. Preferably, one or more of the at least one second container(s) contain(s) a self-sterilising paste of the type described in EP 2 596 812 A1.

Basically, for implementation of the spirit of the invention, it is sufficient to have the dispensing tube arranged opposite from the dispensing plunger with respect to the operative connection. A geometrically exact juxtaposition is not required. The same applies to the closure and the dosing plunger of the at least one second container. As before, the opposite side is given by the transmission of the pressure and therefore no geometrically opposite positioning of the dosing plunger and closure is required in order to implement the spirit of the invention.

A volume compensation element can preferably be implemented through one or two cylinders that are mobile in axial direction in the cylindrical internal space of the first container. Alternatively or in addition, a volume compensation element can just as well be formed through a flexibly deformable skin or membrane.

According to a preferred refinement, the invention can just as well provide that the closure of the at least one second container can be opened by exerting a pressure on the dosing plunger of said second container such that the first container is then connected to said second container.

By this means, the second container or second containers is/are easy to open towards the first container from outside. Simultaneously, the same pressure that opens the closure or closures can be used to transfer the content of the second container or contents of the second containers into the first container. Accordingly, just a single actuation of the dosing plungers or dosing plunger is required to open the closure or closures and to dispense the content of the second container or contents of the second containers into the first container.

It can also be preferred, according to the invention, that the invention provides the closure to be a closure stopper or a closure cap, which, in its closed state, is plugged into an opening in a separating wall between the first container and the at least one second container, such that it closes said opening.

According to a refinement, the invention can provide the mixing facility to comprise at least two mixing vanes that are arranged on the end of the dispensing tube pointing into the inside of the first container and that extend radially from the dispensing tube outwards into the first container.

Mixing vanes shaped as described can ensure that the entire content of the first container is mixed completely.

In this context, the invention can provide the axial height of the mixing vane to be larger than the maximal outer diameter of the closure, whereby the hollow space between the mixing vanes is sufficient to accommodate at least the closure or closures.

This ensures that the closures or closure do/does not block the dispensing tube from being pulled out by being plugged-in between the mixing vanes and the front side of the internal space of the first container which contains the feed-through for the dispensing tube, and prevent the dispensing tube from being pulled out further from the first container.

According to a preferred refinement of the device according to the invention, the invention can provide the device to comprise two second containers, which both are limited on two opposite sides by one closure each and one dosing plunger each for dispensing the content of the second containers.

A third component and/or an additional pharmaceutical agent can be supplied to the cement mixture with said second containers. Preferably, the invention can also provide a third component, preferably an antibiotic or mixture of antibiotics, is or can be filled into a second container by means of a filling aid, such as, for example and preferably according to the invention, a dosing funnel, whereby the filling aid comprises a filling socket that fits to the end of the second container that points away from the first container. Accordingly, according to the invention, the device can comprise said filling aid, which would need to be arranged into the then open end of the second container or of one of the second containers instead of a dosing plunger.

The invention further proposes the at least one closure to be connected to a ring by means of a deformable connection, in particular a flexible fin, whereby the ring is arranged on the inside of the first container such as to be mobile about the dispensing tube such that the connection is axially mobile on the dispensing tube by means of the ring, or whereby the ring is secured to a guide sleeve that is arranged in the feed-through for the dispensing tube of the first container and guides the dispensing tube.

Preferably, according to the invention, the ring as such can be provided to be a sleeve. Having the ring prevents the closure or closures from being freely mobile in the first container and from interfering with the mixing, the mobility of the mixing facility and/or the extrusion of the cement dough. In particular, the closures cannot become placed over the termination opening into the dispensing tube and thus impede the flow of the mixed cement dough.

Alternatively, the closure or closures can just as well be secured to the mixing facility such that the closure or closures, and thus the second container or second containers, are also opened by pushing the dispensing tube into the first container. In order to prevent the at least one second container from opening inadvertently, the invention can provide the dispensing tube to be affixable or affixed, in detachable manner, to the at least one second container by means of a locking device.

In order to prevent inadvertent leakage of bone cement or starting components, the invention can provide an axially mobile core to be arranged in the dispensing tube and to close the dispensing tube on the end pointing into the inside of the first container, whereby, preferably, a circumferential sealing ring is arranged on the core and seals the core with respect to the inner wall of the dispensing tube.

As a result, it can be ensured that no non-finished and non-mixed cement dough enters the dispensing tube from the at least one second container or even leaks from the dispensing tube while the component(s) is/are being mixed and filled in.

The invention also proposes that it is feasible, with the closure opened, that the content of the second container or contents of the second containers can be transferred into the first container by means of the dosing plunger, and that the contents of the first container and second container or second containers can then be mixed with each other in the first container by means of the mixing facility.

This ensures that the device is easy to operate.

To simplify the operation of devices according to the invention, the invention can just as well provide that the dispensing plunger can be or is locked with respect to the first container, preferably can be locked or is locked on the end of the first container opposite from the dispensing tube.

This prevents any inadvertent interfering motion of the dispensing plunger while the first container is being filled and while the first container is being sterilised.

The invention can particularly preferably provide the first container to comprise a cylindrical internal space, and the dispensing plunger in the internal space of the first container to be of a shape that matches the footprint of the cylindrical internal space.

The cylindrical shape is the easiest shape by means of which the first container and thus the device can be implemented. A cylindrical internal space shall be understood geometrically to mean a general cylinder with any footprint, i.e. not just a cylinder with a circular footprint. The internal space can therefore be a straight cylinder having any footprint, i.e. including a non-circular or round footprint. However, a cylindrical internal space having a circular footprint is preferred according to the invention. Said geometry renders all regions of the first container particularly well-reachable for the mixing facility. The dispensing plunger is then also cylindrical and preferably touches against the walls of the cylindrical internal space of the first container by means of a seal. Particularly preferably, a wiper is arranged on the side of the dispensing plunger facing the internal space and serves to prevent the mixed bone cement paste from being pushed past the dispensing plunger and from exiting on the rear of the device when the dispensing plunger is propelled forward. In the case of the preferred circular cylinder geometry of the first container, the mixing facility has mixing vanes that are equal in size or preferably slightly smaller (for example smaller by 0.1 mm) than the internal diameter of the cylindrical internal space.

The cylindrical geometry with a circular footprint is the simplest for the design of the device. It is particularly preferred that the external surface of the first container also is cylindrical accordingly, and that at least 90% of the wall share the same thickness. Then, the first container can essentially be built laterally as a simple tube.

Moreover, the invention can just as well provide the second container or second containers to comprise a cylindrical internal space and can provide the dosing plunger in the internal space of the second container or second containers to be of a shape that matches the foot print of the cylindrical internal space or can provide the dosing plungers to be of a shape that matches the foot print of the corresponding cylindrical internal spaces.

Said symmetry has the same advantages as the symmetry of the first container.

An even more particularly preferred embodiment of the present invention can be implemented by implementing the volume compensation element by means of the dispensing plunger, whereby the dispensing plunger is designed to be made of two parts, i.e. a dispensing plunger in the front and a limiting plunger, which are supported in the first container such as to be mobile with respect to each other, and the motion of the front dispensing plunger out of the first container is limited by the limiting plunger, whereby the limiting plunger can be locked in the first container, whereby the limiting plunger preferably comprises a snap-in mechanism that can be detached from outside and engages an opposite snap-in mechanism on the first container.

Since the dispensing plunger needs to be arranged in the first container such as to be mobile anyway, it can also be utilised as mobile volume compensation element. Accordingly, there is no need to have a separate additional mobile part, which allows the costs of producing the device to be kept low.

In this context, a gas passage opening can be provided in the limiting plunger and/or a gas passage opening can be provided between the limiting plunger and the first container, whereby the gas passage opening(s) is or are well-suited for discharging a gas from and filling a gas in between the front dispensing plunger and the limiting plunger.

This can ensure that the gas between the front dispensing plunger and the limiting plunger can be evacuated and that the intervening space can be sterilised with a sterilising gas. Moreover, a compressed gas can also be supplied into the intervening space in order to push the front dispensing plunger into the inside of the first container in order to extrude the content of the first container and/or the ready-mixed cement dough.

Devices according to the invention, in which the dispensing plunger is used as volume compensation element, can be provided appropriately to have a guide element arranged on the front dispensing plunger that is guided in a matching opening in the limiting plunger, whereby the guide element is preferred to be a cylindrical pin that extends into a matching cylindrical feed-through in the limiting plunger.

As a result of this measure, the front dispensing plunger does not become lodged or cants while moving and does not block further motion in the first container.

A further refinement of the invention proposes a detachable locking element to block an axial motion of the front dispensing plunger with respect to the limiting plunger while the device is in its storage condition.

As a result, any filling of the first container and any sterilisation of the device is not made more difficult by the two parts (the front dispensing plunger and the limiting plunger) moving with respect to each other.

A refinement of the present invention proposes the front dispensing plunger to be supported, such as to be mobile, with respect to the limiting plunger by means of an elastic spring, whereby the spring is arranged between the front dispensing plunger and the limiting plunger and pushes the front dispensing plunger into the internal space of the first container. Preferably, the spring is arranged about the guide element and/or the pin if either of these is present.

As a result, the front dispensing plunger is actively restored to the desired position by the elastic spring upon repeated changes of the volume of the first container, which may be caused, for example, by mixing the content of the first container by repeatedly pushing and pulling the dispensing tube with the mixing facility in and out.

It is particularly advantageous, according to the invention, to provide the space between the shiftable dispensing plunger and the limiting plunger to have a volume that is at least equal in size to the sum of, firstly, the difference in volume between the volume of the part of the dispensing plunger that is situated in the first container when the dispensing tube is fully inserted into the first container and when the dispensing tube is fully pulled out of the first container plus, secondly, the volume of the second component or the volume of the internal space of the one second container or the volumes of the internal spaces of the second containers.

This structure ensures that the dispensing plunger, as volume compensation element, can accommodate the full change of volume of the content of the first container.

A further refinement of the invention, preferred according to the invention, can provide at least one volume compensation element to be supported as in a bearing by means of an elastic spring such as to be mobile with respect to the first container, whereby the spring pushes the volume compensation element in the direction of the internal space of the first container.

As a result, the volume compensation element is actively restored to the original position by the elastic spring upon repeated changes of the volume of the first container which are arise due to the mixing of the content of the first container by repeatedly pushing and pulling the dispensing tube with the mixing facility in and out.

The invention also proposes to arrange at least one porous gas-permeable sealing ring on the external surface of the at least one dosing plunger such that a gas exchange between the space formed by the inner walls of the at least one second container, the closure, and the dosing plunger, and the surrounding atmosphere can take place.

The invention can also provide, alternatively or in addition, the dosing plunger to comprise at least one gas-permeable porous disc such that a gas exchange between the space formed by the inner walls of the at least one second container, the closure, and the dosing plunger, and the surrounding atmosphere can take place.

As a result, the content of the at least one second container can be evacuated and sterilised with a sterilising gas.

Another refinement of the present invention can provide the at least one dosing plunger to possess at least one directional snap-in element that can engage the at least one opposite snap-in mechanism on the inner surface of the second container in appropriate manner such that, after snapping-in takes place, a backward motion of the dosing plunger out of the second container(s) cannot take place.

This ensures that, upon extrusion of the ready-made cement mixture by means of the dispensing plunger, the cement mixture is dispensed exclusively through the dispensing tube and does not leak through the at least one second container.

Moreover, the invention proposes to arrange the at least one second container for the at least one second component of the bone cement on the first container on the same side as the feed-through for the dispensing tube, in particular adjacent to the feed-through for the dispensing tube.

This design simplifies the operation of the device. This applies especially when the dispensing plunger is used as volume compensation element and when a screw cap, screwed onto a thread about the dispensing tube or about the feed-through for the dispensing tube, is used to propel the dosing plungers.

A refinement of the present invention also proposes to insert a separate third hollow cylinder into the at least one second container, which preferably is arranged on the head of the first container, whereby the third hollow cylinder contains a component of the bone cement and is closed by means of a dosing plunger and a closure stopper.

Preferably, the closure stopper is connected to the second hollow cylinder by means of a mobile fin.

This measure simplifies the production of the device since the separate third hollow cylinder can be filled with a component of the bone cement and/or an additive for the bone cement, and since the separate third hollow cylinder needs to be inserted into one of the second containers only after it is filled.

The invention can just as well provide a separate hollow cylinder to be arranged in a second container, which is arranged on the head (i.e. in the front) of the first container, and to contain a third component of the bone cement and to be closed by means of a closure stopper and a dosing plunger, whereby the closure stopper is connected to the first hollow cylinder by means of a mobile fin, and to arrange a further separate hollow cylinder in a further second container, which is arranged on the head of the first container, and to contain a pharmaceutical agent and to be closed by means of a closure stopper and a dosing plunger, whereby the closure stopper is connected to the second hollow cylinder by means of a mobile fin.

Moreover, the invention proposes the axially mobile dispensing plunger to possess a guide element that engages a guidance of the dispensing plunger.

In this context, the invention can also provide the second dosing plunger to possess a guidance for the guide element of the dispensing plunger and the second dosing plunger to possess at least one snap-in element that can be detached by applying external pressure and affixes the second dosing plunger to the inside wall of the first container in reversible manner.

The objects of the present invention are also met through a method for producing a polymethylmethacrylate bone cement (PMMA bone cement) using a device according to any one of the preceding claims, characterised by the steps of:

A) providing the device, whereby the first container is filled with a first liquid or pasty component of the PMMA bone cement and the at least one second container is filled with a second component of the PMMA bone cement, which preferably is powdery or pasty;

B) opening the at least one second container by pushing the dosing plunger forward and dispensing the second component from the at least one second container into the first container by further propelling the dosing plunger forward, whereby the change of volume of the content of the first container upon the introduction of the second component into the first container is compensated for through a motion of the at least one volume compensation element; and C) mixing the two components in the first container through moving the mixing facility, whereby moving the mixing facility is associated with the dispensing tube connected to the mixing facility being pushed into and pulled out of the first container repeatedly, whereby the change of volume of the content of the first container during mixing is compensated for through a motion of the at least one volume compensation element.

In this context, the invention can provide a core to be removed from the dispensing tube after step C), and then a step D) to take place, in which the mixed bone cement is applied by propelling the dispensing plunger forward in the first container through the dispensing tube.

Moreover, a refinement of the method according to the invention proposes that the content of the first container is mixed by moving the mixing facility, which is connected to the dispensing tube, in the first container by moving the dispensing tube into and out of the first container, whereby, in addition, the mixing facility preferably is being rotated in the first container by rotating the dispensing tube.

As a result, the method can be implemented particularly easily, since only one mobile element, i.e. the dispensing tube, is being operated such that the likelihood of incorrect operation is reduced. Moreover, it is easy to mix the components even under adverse conditions outside of an orderly surgical room.

Moreover, methods according to the invention can be provided such that the interior of the first container and the interior of the at least one second container are de-gassed and sterilised before step A) takes place, whereby it is preferred for this purpose to lock the limiting plunger, the front dispensing plunger and/or the volume compensation element, and subsequently the first container is filled with a first component of the bone cement and the at least one second container is filled with a second component of the bone cement, whereby it is preferred, concurrently or subsequently, to fill an antibiotic or a mixture of antibiotics into at least one second container.

This ensures the sterility of the content. This allows infections of the patient to be prevented.

According to a preferred refinement of the method according to the invention, the invention can just as well provide the dispensing tube, after mixing, is moved out (or pulled out) in the direction out of the first container such that the mixing facility touches against the front inner surface of the first container.

Moreover, the invention can provide the dosing plunger or dosing plungers, after being pushed in completely, to be affixed irreversibly against the at least one second container by means of a snap-in mechanism.

Methods according to the invention can therefore provide the implementation of the method to involve the compensation of changes of volume occurring in the first container by the volume compensation element.

Provided the dispensing plunger is lockable by a locking element, the invention can provide the locking element of the dispensing plunger to be detached, such that the dispensing plunger is freely mobile in axial direction, before the content of the at least one second container is transferred to or introduced into the first container.

The invention is based on the surprising finding that designing the device according to the invention and using the method according to the invention allows to easily provide an option for mixing and application of a bone cement whose individual components have a disparate mixing ratio of 1:10 and more. Providing second containers or a second container that are or is easy to handle and easily accessible and contain(s) the lower dosed component, said component can be added by the user easily and with little effort. Due to the volume compensation element, the cement paste or the starting components can be prevented from leaking from the device and from thus contaminating the surroundings and/or the bone cement when they are being combined. The structure can be manufactured, sterilised, and filled with the starting components both easily and inexpensively. Moreover, providing a dosing funnel can enable the user to add further additives such as, for example, a special mixture of antibiotics or other pharmaceutical agents customised for the patient.

One example of the structure of a device according to the invention is, for example, a device for storing and mixing polymethylmethacrylate bone cement composed of a) a cylindrical storage container comprising a first container that is filled with pasty component A;

b) a dispensing tube that can be moved axially through a feed-through on the head of the dispensing container, whereby the dispensing tube contains two or more mixing vanes on the side facing the first container;

c) a core plugged into the dispensing tube that closes, in reversible manner, the dispensing tube on the side of the tube facing the first container;

d) at least one hollow cylinder that is connected to the first container, whereby the hollow cylinder forms a second container that is filled with component B;

e) a closure stopper that can be pushed out axially only in the direction of the first container and separates the first container from the second container;

f) at least one dosing plunger that is arranged in the at least one hollow cylinder such as to be axially mobile;

g) whereby the second container is limited in the hollow cylinder by means of the closure stopper and the dosing plunger;

h) an axially shiftable dispensing plunger (the front dispensing plunger) that limits the first container;

i) a second plunger (the limiting plunger) that is arranged behind the front dispensing plunger, whereby said second plunger is affixed on the inner cartridge wall (the first container) by means of a snap-in element that can be detached by an external influence, whereby the second plunger possesses at least one gas passage opening that connects the space of the first container between the axially shiftable front dispensing plunger and the surrounding atmosphere; and j) whereby the volume of the space between the shiftable front dispensing plunger and the second limiting plunger is at least equal in size to the sum of the volumes of component B and the dispensing tube when the dispensing tube is at maximal immersion depth in the first container.

It is preferred in this context to provide two hollow cylinders with one closure stopper and one axially mobile dosing plunger each.

A method according to the invention can be implemented, for example, through a) firstly, detaching the locking element of the dispensing plunger such that the dispensing plunger is freely mobile in axial direction;

b) by pushing the at least one dosing plunger in the direction of the closure stopper, whereby the stopper exits from the hollow cylinder into the first container, in which pasty component A is situated, and pressing component B into the first container into pasty component A by moving the dosing plunger further;

c) by affixing, by means of the snap-in mechanism, the dosing plunger irreversibly in the hollow cylinder after it reaches the inside of the head of the storage container;

d) subsequently mixing component B and pasty component A to form cement dough C by moving the dispensing tube axially and tangentially by means of the mixing vanes;

e) moving the dispensing tube in the direction of the head of the storage container, after the mixing took place, such that the mixing facility touches against the inner surface of the storage container (the first container);

f) by then pulling the core out of the dispensing tube and then moving the limiting plunger and the front dispensing plunger situated above it in the direction of the head of the storage device, whereby cement dough C is extruded from space through the dispensing tube into the surroundings; and by g) compensating for the changes of volume of the first container during steps b, c, and d, which are caused by component B being squeezed in and by the dispensing tube including the mixing vanes being pushed in and pulled out, through axial motions of the front dispensing plunger.

Another method according to the invention can be implemented, for example, through a) firstly, detaching the locking element of the dispensing plunger such that the dispensing plunger is freely mobile in axial direction;

b) by pushing the first dosing plunger in the direction of the closure stopper, whereby the stopper exits from the hollow cylinder into the first container, in which pasty component A is situated, and pressing a pharmaceutical agent into the first container into pasty component A by moving the first dosing plunger further;

c) by affixing, by means of the snap-in mechanism, the first dosing plunger irreversibly in the hollow cylinder after it reaches the interior of the head of the storage container;

d) by then pushing the second dosing plunger in the direction of the closure stopper, whereby the stopper exits from the hollow cylinder into the first container, in which pasty component A is situated, and by pressing component B1 into the first container into pasty component A by moving the second dosing plunger further;

e) by affixing, by means of the snap-in mechanism, the dosing plunger irreversibly in the hollow cylinder after it reaches the interior of the head of the storage container;

f) by subsequently mixing component B1 and the pharmaceutical agent and pasty component A to form cement dough C by moving the dispensing tube including the mixing facility axially and tangentially;

g) by moving the dispensing tube in the direction of the head of the storage container, after the mixing took place, such that the mixing facility touches against the inner surface of the storage container;

h) by then pulling the core out of the dispensing tube and then moving the limiting plunger and the front dispensing plunger situated above it in the direction of the head of the storage device, whereby cement dough C is extruded from the first container through the dispensing tube into the surroundings; and i) by compensating for the changes of volume of the first container during steps b, c, and d, which are caused by the pharmaceutical agent and component B1 being squeezed in and by the dispensing tube including the mixing vanes being pushed in and pulled out, through axial motions of the front dispensing plunger.

BRIEF DESCRIPTION OF THE DRAWINGS

Further exemplary embodiments of the invention shall be illustrated in the following on the basis of eight schematic figures, though without limiting the scope of the invention. In the figures:

FIG. 5 shows a schematic perspective cross-sectional view of the device shown according to FIGS. 3 and 4, in which a dosing plunger is pushed in;

FIG. 8 shows a schematic side view of a device according to the invention with a dosing plunger pushed in.

For simplification, identical or similar components in the figures are identified through the same reference numbers to some extent. Sectioned surfaces are shown by hatching.

FIG. 1 shows a schematic side view of a device 1 according to the invention, and FIG. 2 shows a schematic side view of the device 1 according to FIG. 1 rotated by 90°. Device 1 is a bone cement cartridge system 1 for retaining, storing, mixing, and applying a bone cement and/or the components thereof. Device 1 and the parts thereof are essentially made of plastic material, for example by means of injection moulding. Device 1 comprises a cylindrical first container 2 that has a cylindrical internal space. A pasty first component and/or a main component of a medical multi-component bone cement, preferably of a PMMA bone cement, is present in the internal space of the first container 2.

Figure 1:
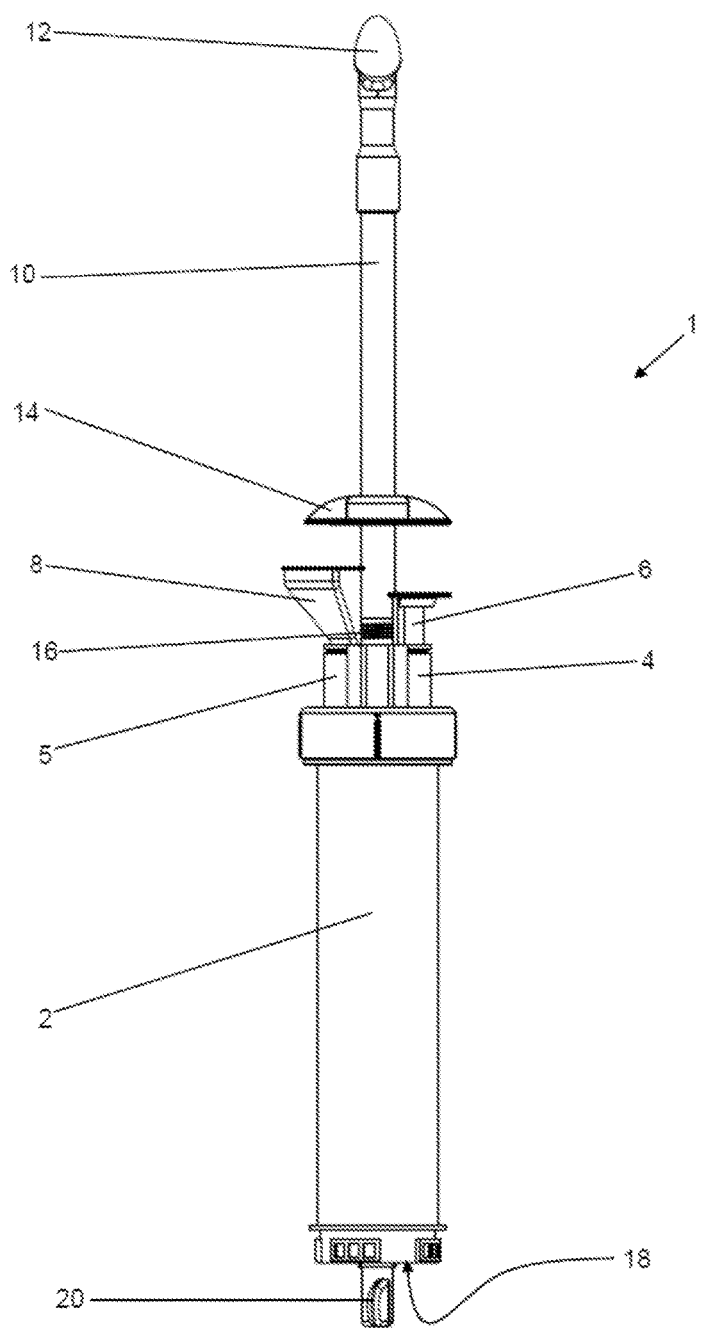
FIG. 1 shows a schematic side view of a device according to the invention with a filling funnel inserted.
Figure 2:
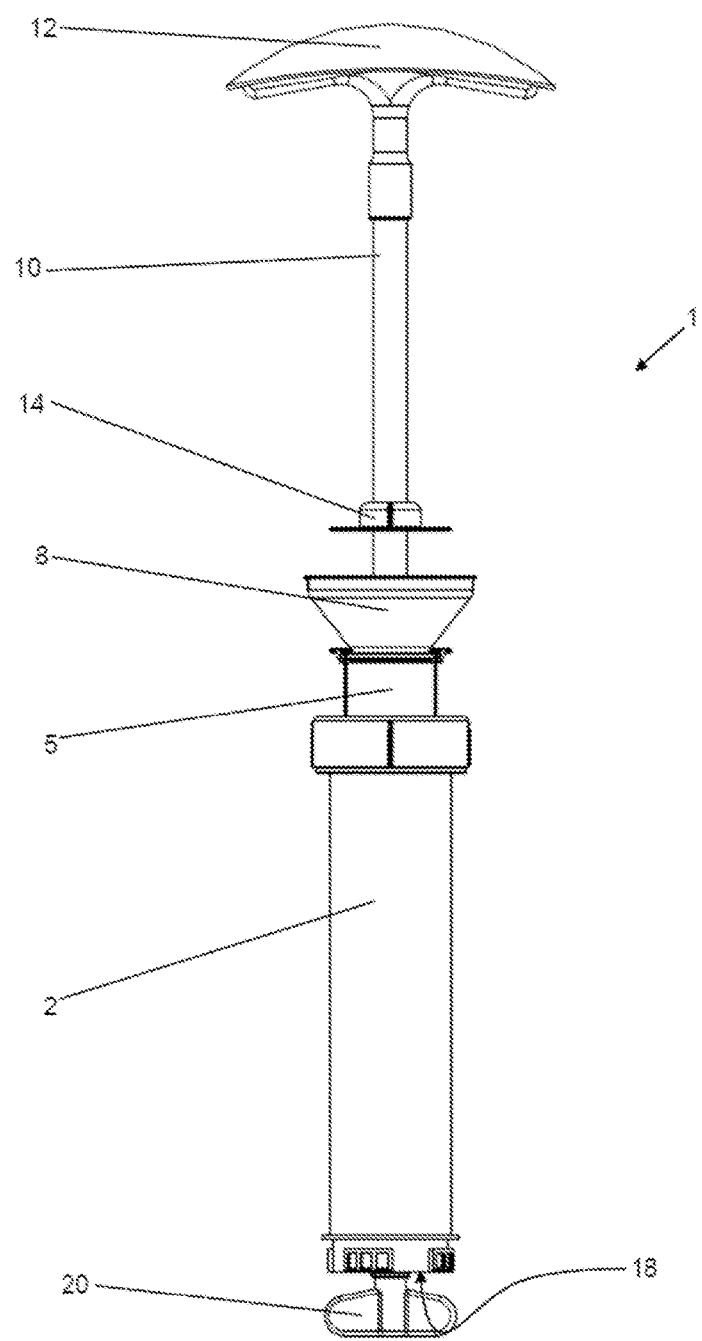
FIG. 2 shows a schematic side view of the device according to FIG. 1 rotated by 90°.

Two further (second) containers 4, 5 are arranged on the front of the first container 2 (on the top in FIGS. 1 and 2) and are each connected to the first container 2 by means of an opening (not shown), whereby closures (not shown) are arranged in the two openings that close the openings and thus separate the first container 2 from the two containers 4, 5 and/or the internal spaces thereof. Said second container 4 is closed by means of a dosing plunger 6 on the side of the second container 4 opposite to the opening. The first second container 4 is filled with a second component of the bone cement that can be powdery or pasty.

The second dosing plunger (not shown) of the other second container 5 has been taken out and a dosing funnel 8 has been inserted into the thus opened other second container 5 (the second second container 5) by means of which a pharmaceutical agent (such as, for example, an antibiotic), a mixture of agents, a further component of the bone cement or a mixture thereof can be filled into the other second container 5. Subsequently, the second dosing plunger is inserted in the same manner as the first dosing plunger 6. The dosing funnel 8 allows additional components and agents to be filled in shortly before the application during a surgery.

A dispensing tube 10 is guided through a gas-tight feed-through (not shown) of the first container 2, between the two openings of the second containers 4, 5 and/or between the two second containers 4, 5 into the first container 2. The dispensing tube 10, by means of which the finished bone cement mixture is being applied, is mobile in longitudinal direction (from top to bottom and vice versa in FIGS. 1 and 2) and is supported in the gas-tight feed-through like in a bearing such that it can rotate. On the inside of the first container 2, a mixing facility (not shown) is arranged on the dispensing tube 10 in the form of two or more mixing vanes that extend radially away from the dispensing tube 10 in the direction of the inner walls of the first container 2 to or almost to the inner walls of the first container 2. As a result, the dispensing tube 10 can be moved in order to mix the content of the first container 2. The front opening (on the top in FIGS. 1 and 2) of the dispensing tube 10 is closed by means of a handle part 12. The handle part 12 is connected to a rod on the inside of the dispensing tube 10 that extends up to a core (not shown) on the end of the dispensing tube 10 that points towards the inside of the first container 2, and is connected to said core. The core seals the dispensing tube 10. The dispensing tube 10 preferably consists of a transparent plastic material such that it can be recognised from outside how far the mixed bone cement dough already advanced in the dispensing tube 10 when the finished bone cement mixture is being applied through the dispensing tube 10.

The core can be pulled out of the dispensing tube 10 by means of the handle part 12 and the rod to open the dispensing opening, i.e. the device 1 is thus made ready for application of the mixed bone cement dough.

A screw cap 14 having an internal thread (not shown) is arranged about the dispensing tube 10 and can be screwed onto a matching external thread 16 on the front of the first container 2. Provided the dosing plungers 6 are plugged-in into both containers 4, 5, the dosing plungers 6 can be pushed into the second containers 4, 5 by placing-on the screw cap 14, by pressing-on the screw cap, and by screwing-on the screw cap 14. The content of the two second containers 4, 5 thus transmits a pressure acting on the closures of the two second containers 4, 5 to the first container 2 such that the closures in the openings to the first container 2 are detached from said openings and are pushed into the first container 2. This opens the two second containers 4, 5 towards the first container 2.

Figure 8:
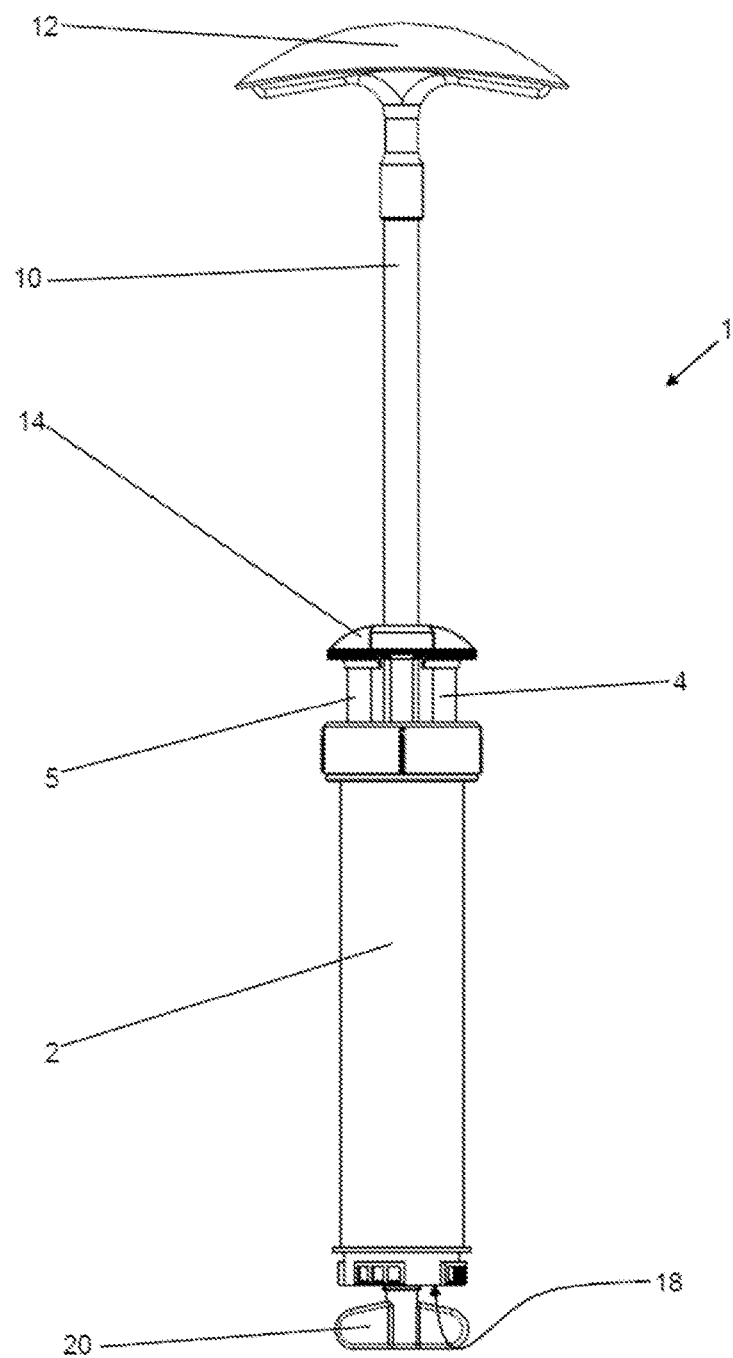

Propelling the dosing plungers 6 further transfers the content of the two second containers 4, 5 into the content of the first container 2. FIG. 8 shows a side view of the device 1 with the dosing plunger 6 being pushed-in to the full extent. The resulting increase in volume in the first container 2 is taken up by means of a volume compensation element.

Presently, a two-part dispensing plunger 18, inserted on the floor-side (on the bottom in FIGS. 1 and 2) into the first container 2, is provided as volume compensation element. The first front dispensing plunger (not shown) of the dispensing plunger 18, which points further into the inside of the first container 2, is supported like in a bearing such as to be mobile in the longitudinal direction of the symmetry axis of the first container 2. A steel spring (not shown) pushing the front dispensing plunger into the inside of the first container 2 is arranged between the floor-side second part (the limiting plunger) of the dispensing plunger 18 and the front dispensing plunger of the dispensing plunger 18. Provided as volume compensation element, the dispensing plunger 18 is thus capable of taking up volume changes caused by the contents of the second containers 4, 5 being filled in, as well as those volume changes generated by the dispensing tube 10 being pushed in and pulled out of the first container 2. The function of the two-part dispensing plunger 18 is illustrated in more detail through FIG. 6 and FIG. 7.

A butterfly screw 20 for operation of a locking element is provided on the dispensing plunger 18, whereby the two parts of the dispensing plunger 18 can be locked to each other in detachable manner by rotating the butterfly screw 20 such that the front dispensing plunger and the limiting plunger are no longer axially mobile with respect to each other. The locking is advantageous for filling of the first container 2 and for sterilising by evacuation and filling with a sterilising gas. In order to prevent the front dispensing plunger from moving inadvertently, the locking element preferably stays closed until right before the contents of the two second containers 4, 5 are introduced into the first container 2. The butterfly screw 20 is pulled out and removed prior to dispensing the ready-mixed cement dough from the device 1 and/or the dispensing plunger 18. The limiting plunger then has a rear-side surface onto which a pestle of a cement gun can exert a pressure in order to propel both parts of the dispensing plunger 18 and thus expel the content (the finished bone cement) from the first container 2. Alternatively, just the front dispensing plunger can be propelled by means of a compressed gas. For this purpose, one or more gas feed-throughs must be present in the limiting plunger.

Figure 3:
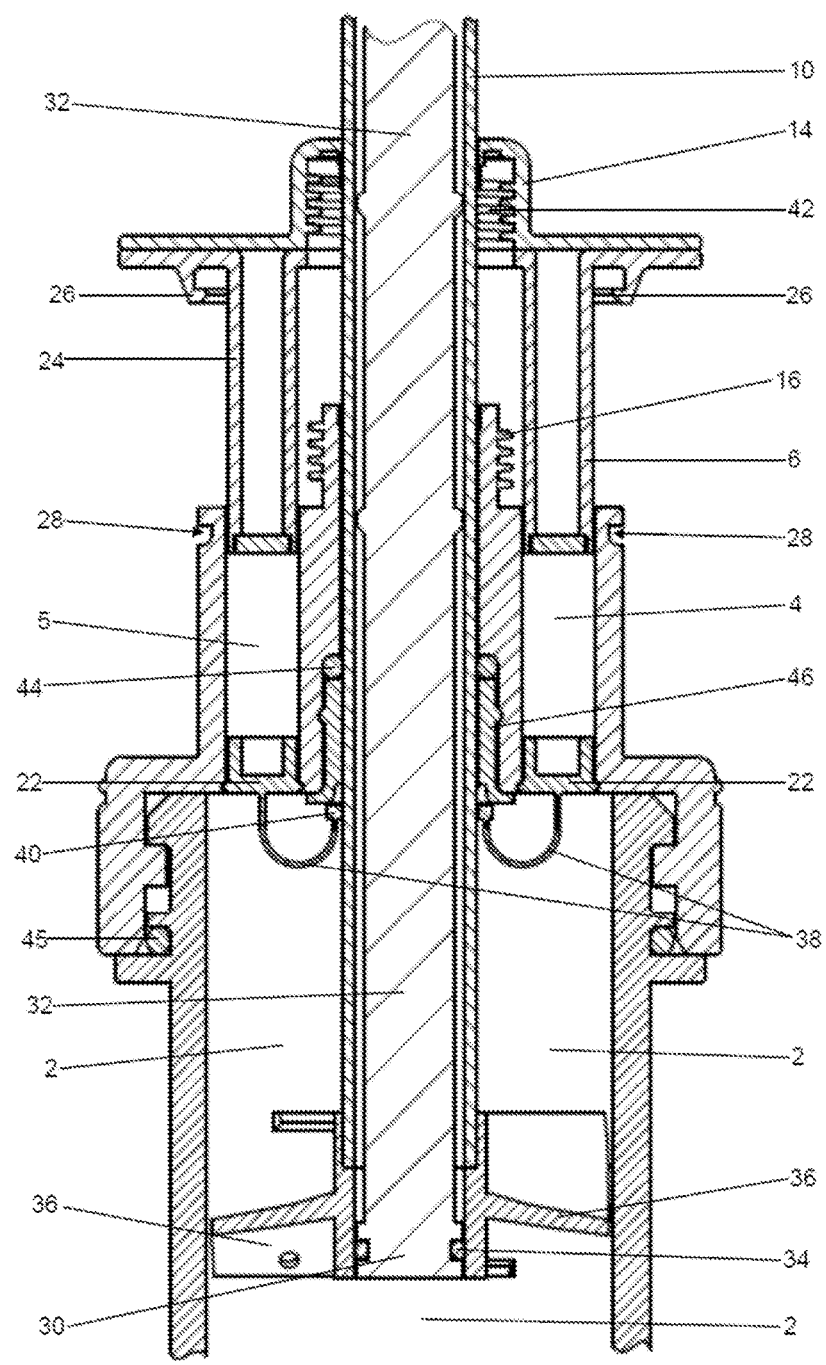
FIG. 3 shows a schematic cross-sectional view of a part of a device according to the invention.
Figure 4:
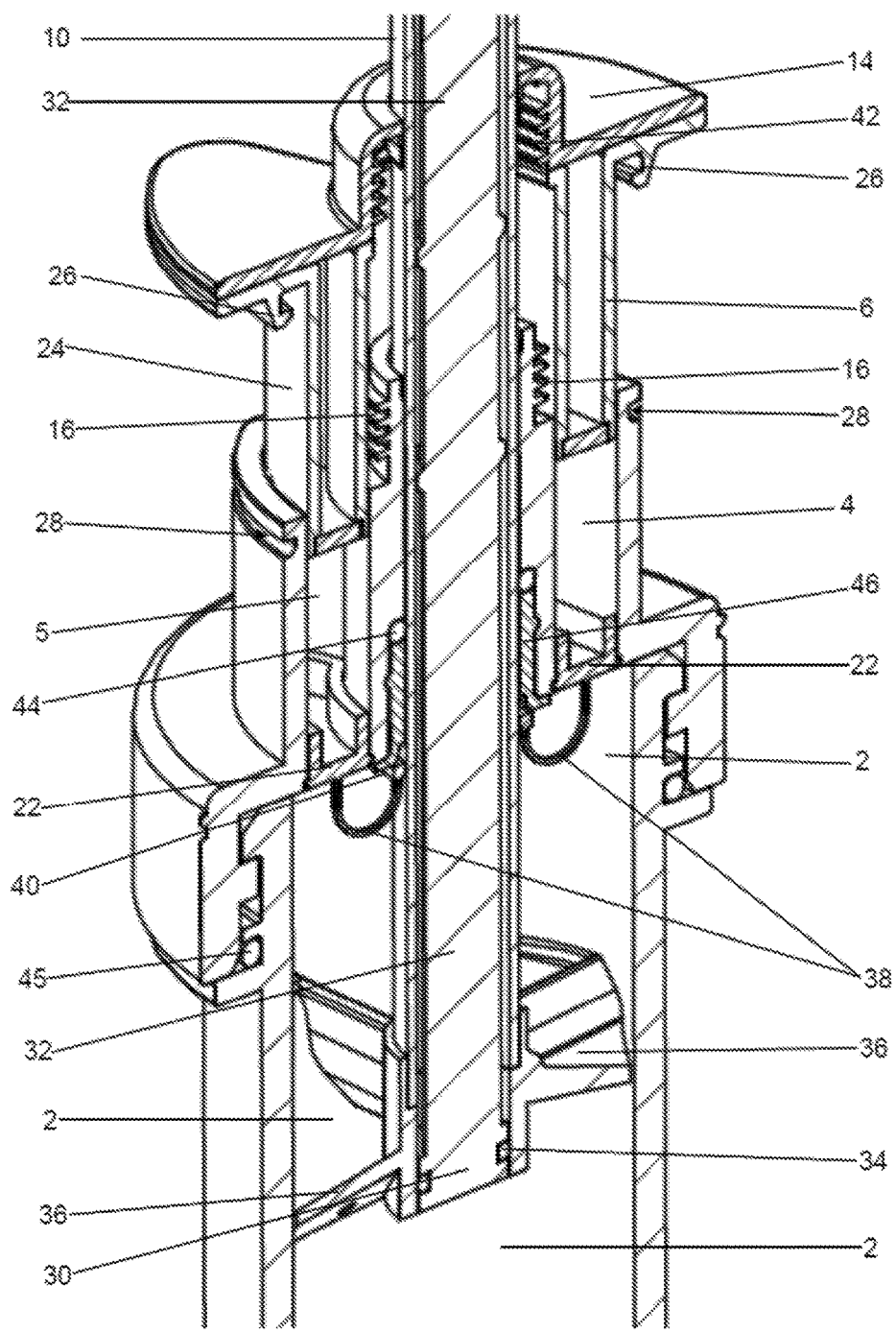
FIG. 4 shows a schematic perspective cross-sectional view of the device shown in FIG. 3.

FIG. 3 shows a magnified schematic cross-sectional view of a part of the device 1 according to the invention, and FIG. 4 shows a schematic perspective cross-sectional view of the part shown in FIG. 3. Device 1 comprises a first container 2 that has a cylindrical internal space. A cylindrical dispensing plunger (not shown in FIGS. 3 to 5), which fits in the direction of the symmetry axis and/or longitudinal axis of the internal space of the first container 2 and is mobile, but detachably lockable, is arranged on the floor-side in the cylindrical internal space (on the bottom in FIGS. 3 to 5).

The front side (on the top in FIGS. 3 to 5) of the first container 2 is partly covered by two second containers 4, 5. A stopper 22 is provided in each of the openings of the second containers 4, 5 towards the first container 2 and separate the second containers 4, 5 from the first container 2, or separate the internal spaces thereof, as the case may be. The two second containers 4, 5 are closed on their front by two dosing plungers 6, 24. The external shape of the dosing plungers 6, 24 corresponds to the inner shape of the second containers 4, 5 and the dosing plungers 6, 24 can be shifted in longitudinal direction of the second containers 4, 5 (from top to bottom in FIGS. 3 to 5) such that the contents of the second containers 4, 5 can be pressed into the first container 2 by means of the dosing plungers 6, 24.

The two second containers 4, 5 and the dosing plungers 6, 24 are cylindrical and have a kidney-shaped footprint, i.e. a kidney-shaped cross-section perpendicular to the cylinder axis, and are arranged about the dispensing tube 10 to be adjacent to each other.

Figure 5:
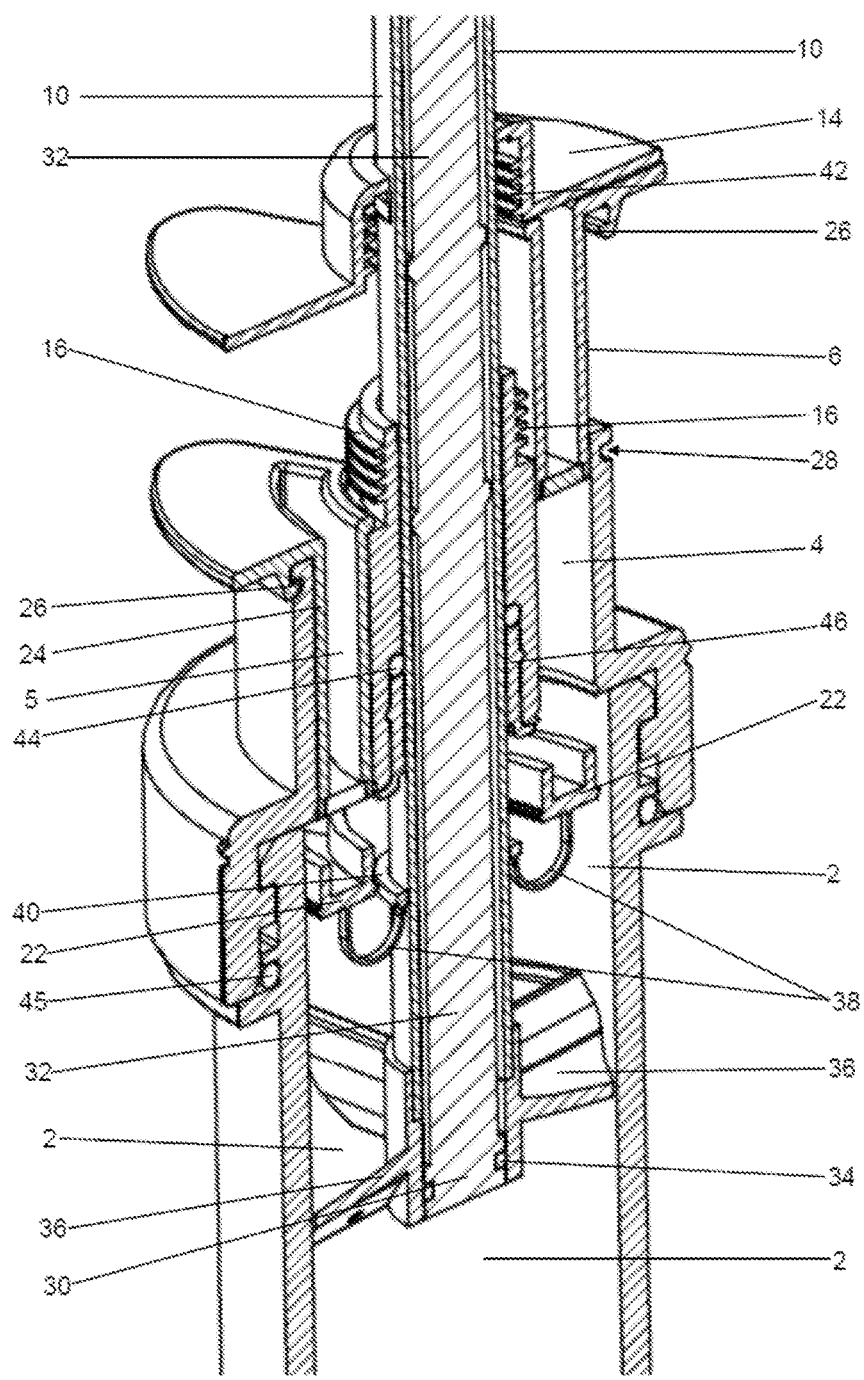

Pushing the dosing plungers 6, 24 inwards pushes the stoppers 22 out of the openings to the first container 2. Then the content of the second containers 4, 5 is pushed into the first container 2. In this context, FIG. 5 shows a schematic perspective cross-sectional view of the part of device 1 that is also shown in FIGS. 3 and 4, in which a dosing plunger 24 is pushed in fully into one of the second containers 5. Snap-in elements 26 are provided on the top of the dosing plungers 6, 24 and engage opposite snap-in mechanisms 28 on the outer surface of the second containers 4, 5. As soon as the dosing plungers 6, 24 are pushed in fully, the snap-in elements 26 snap into the opposite snap-in mechanisms 28 such that the dosing plungers 6, 24 can no longer be moved out of the second containers 4, 5. This ensures that the finished bone cement mixture cannot be extruded into and through the second containers 4, 5 when the content of the first container 2 is being pressed out by means of the dispensing plunger.

Instead, the finished bone cement mixture is extruded through the dispensing tube 10 and can be applied by means of the tip thereof to the bone of a patient during surgery. For this purpose, a core 30 that closes the dispensing tube 10 from inside must first be pulled out of the dispensing tube 10 by means of a rod 32 that is connected to the core 30. The core 30 is sealed with respect to the inner wall of the dispensing tube 10 by means of a circumferential seal 34 such as, for example, an O-ring made of rubber. The core 30 is situated on the end of the dispensing tube 10 that points into the inside of the first container 2.

This end of the dispensing tube 10 also has mixing vanes 36 arranged on it, which extend radially away from the dispensing tube 10 in the direction of the inner walls of the first container 2 and approach the same up to 0.1 mm or even more closely.

The two stoppers 22 are connected by means of two fins 38 to a ring 40 that is arranged about the dispensing tube 10. Having the fins 38 and ring 40 present ensures that the stoppers 22 cannot move freely in the first container 2 and, in the process, prevent or impair the mixing of the content of the first container 2 by means of the mixing facility 36. Moreover, having the ring 40 and fins 38 prevents the stoppers 22 from inadvertently becoming placed in front of the junction leading into the dispensing tube 10, which would impair the flow of the finished bone cement mixture into the dispensing tube 10.

A screw cap 14 is arranged in front of the two dosing plungers 6, 24 such that it can rotate about the dispensing tube 10. The screw cap 14 has an internal thread 42 that can be screwed onto an external thread 16 in front of the two second containers 4, 5, whereby the dosing plungers 6, 24 are pushed into the second containers 4, 5 during this process. The dosing plungers 6, 24 comprise gas-permeable openings (not shown).

The various individual parts of the device 1 are sealed with respect to each other by sealing rings 44, 45 made of rubber such that the first container 2 can be evacuated and such that the content of the first container 2 cannot be extruded through the intervening spaces when a pressure is applied by means of the dispensing plunger.

The dispensing tube 10 is guided through a guide sleeve 46 into the first container 2 and is sealed by means of a sealing ring 44. The head of the cartridge (of the first container 2) at which the two second containers 4, 5 are provided, is plugged, in the way of a cap, onto the cylinder by means of a snap-in mechanism that forms the wall of the first container 2, and on the guide sleeve 46. The head of the cartridge is sealed with respect to the cylinder wall of the first container 2 by means of a sealing ring 45.

Figure 6:
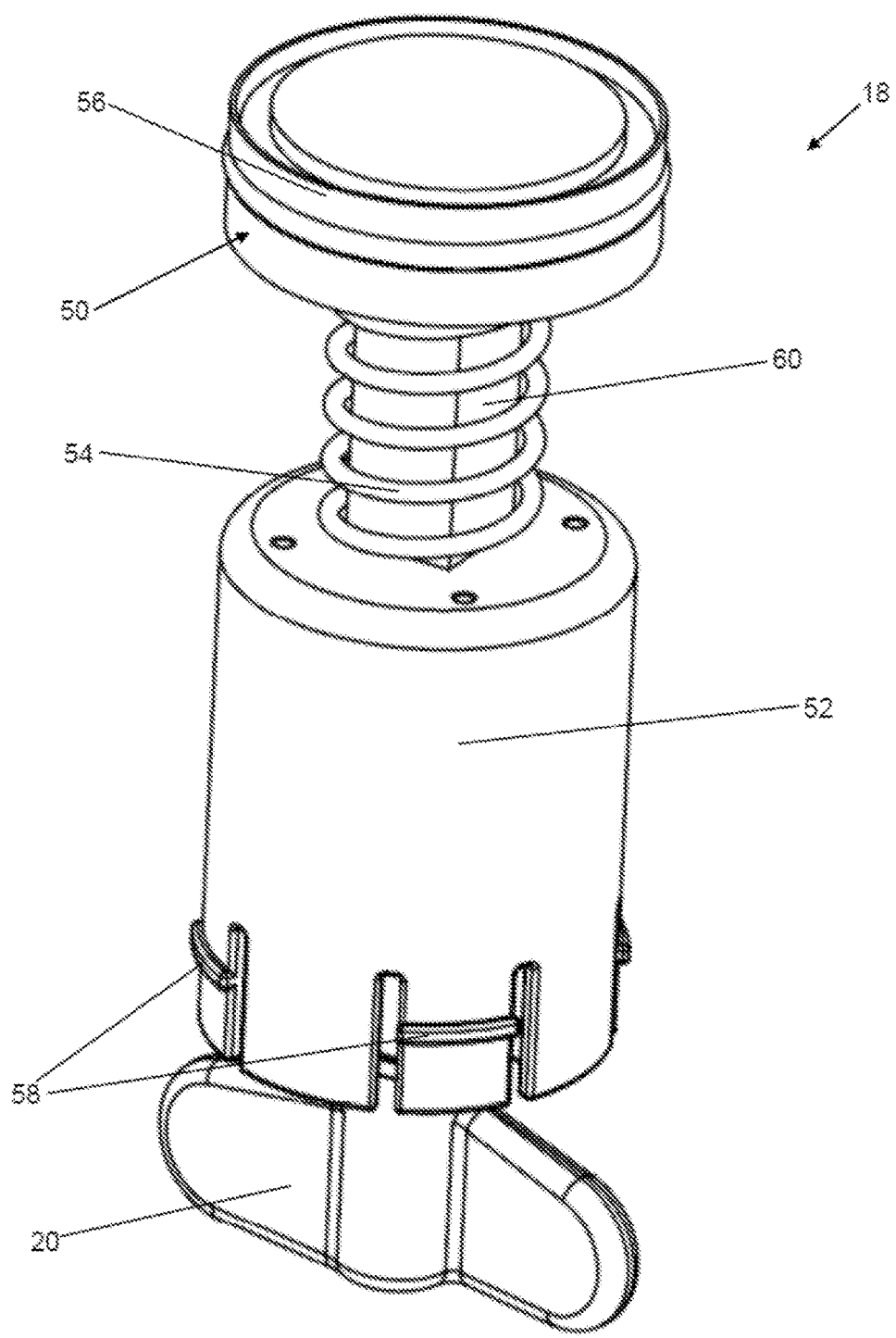
FIG. 6 shows a schematic perspective view of a two-part dispensing plunger, designed as volume compensation element, for a device according to the invention.
Figure 7:
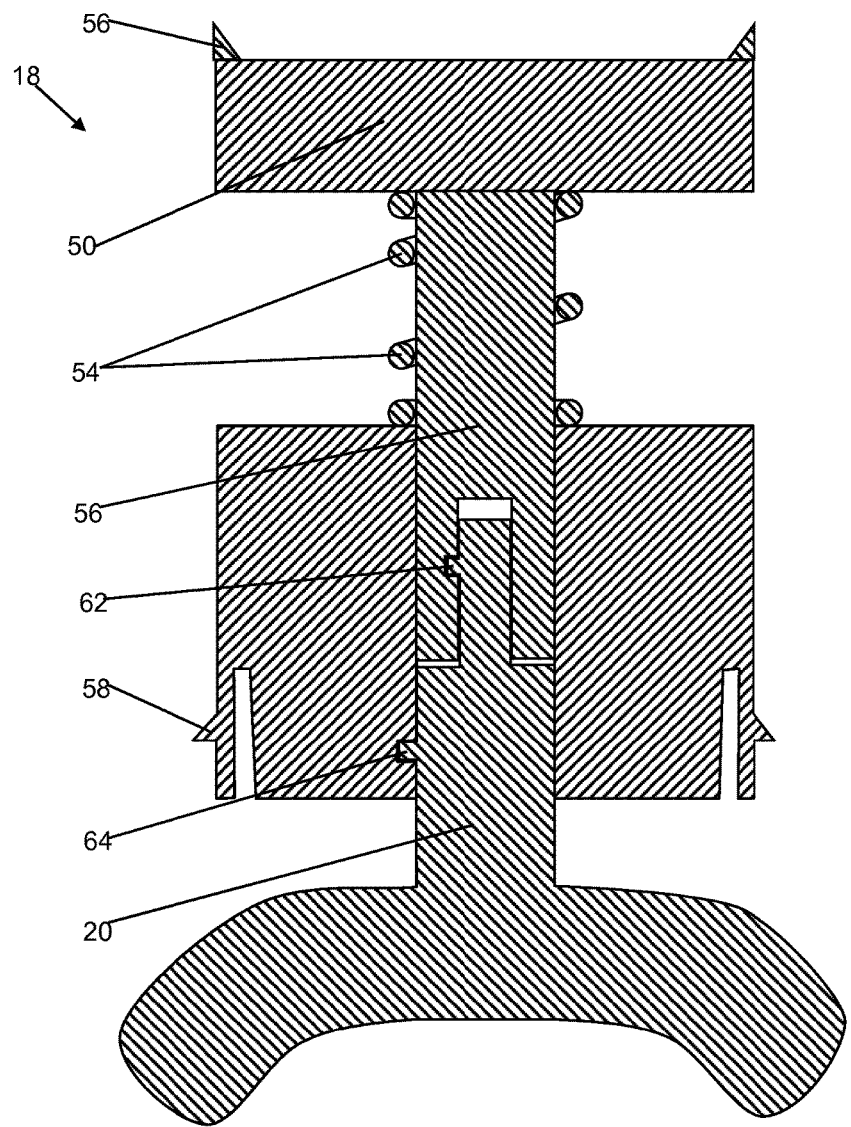
FIG. 7 shows a schematic cross-sectional view of a two-part dispensing plunger, designed as volume compensation element, for a device according to the invention.

FIG. 6 shows a schematic perspective view of a two-part dispensing plunger 18 of a device according to the invention that is provided as volume compensation element, and FIG. 7 shows a schematic cross-sectional view of a two-part dispensing plunger 18 that is provided as volume compensation element, in the manner in which it can be inserted into the devices 1 according to FIGS. 1 to 5 and 8. The first part on the front (on the top in FIG. 6) of the dispensing plunger 18, i.e. the front dispensing plunger 50, is supported, such as to be mobile, against the second part in the rear, i.e. the limiting plunger 52 of the dispensing plunger 18. An elastic spring 54 made of steel or made of an elastic plastic material is arranged between the two parts 50, 52 of the dispensing plunger 18 and pushes the front dispensing plunger 50 into the interior of the first container, i.e. upwards in FIGS. 6 and 7.

The limiting plunger 52 has a gas-permeable feed-through (not shown) provided in it that enables the air to escape from the intervening space between the two parts 50, 52 in order to allow the intervening space to be sterilised with a sterilising gas and, if applicable, in order to propel the front dispensing plunger 50 by means of a gas pressure without having to move the limiting plunger 52. A circumferential wiper lip 56 is arranged on the upper edge of the front dispensing plunger 50. The wiper lip 56 touches against the inner walls of the first container 2, while the front dispensing plunger 50 is inserted into the first container 2, and ensures that no residual bone cement stays behind in the first container 2 and/or that no bone cement can leak from the rear of the device 1.

A locking element that can be detached by means of a butterfly screw 20 can be used to lock the front dispensing plunger 50 with respect to the limiting plunger 52. Multiple snap-in elements 58, which are arranged on the outer circumference of the limiting plunger 52 and are bendable radially inward, such as projecting springs and/or strips, connect the limiting plunger 52 to opposite snap-in means (not shown) that are arranged correspondingly on the inner walls of the first container 2, such as, for example, a circumferential groove, such that the limiting plunger 52, once inserted, can no longer be removed easily from the first container 2.

A butterfly screw 20 for operation of the locking element is provided on the dispensing plunger 18, whereby the two parts 50, 52 of the dispensing plunger 18 can be locked to each other in detachable manner by rotating the butterfly screw 20 such that the front dispensing plunger 50 and the limiting plunger 52 are no longer axially mobile with respect to each other. The locking mechanism is advantageous for filling of the first container 2 and for sterilising of the intervening space between the two parts 50, 52 by evacuation and filling-in a sterilising gas. In order to prevent the dispensing plunger 50 from moving inadvertently with respect to the limiting plunger 52, the locking element preferably stays closed until right before the contents of the two second containers 4, 5 are introduced into the first container 2.

The butterfly screw 20 is pulled out and removed prior to dispensing the ready-mixed cement dough from the device and/or the dispensing plunger 18. The limiting plunger 52 then has a rear-side surface onto which a pestle of a cement gun can exert a pressure in order to propel both parts 50, 52 of the dispensing plunger 18 and thus expel the content (the finished bone cement mixture) from the first container 2. Alternatively, just the front dispensing plunger 50 can be propelled by means of a compressed gas. For this purpose, one or more gas feed-throughs must be present in or adjacent to the limiting plunger 52.

A guide element 60 in the form of a cylindrical pin having a square or rectangular footprint is attached on the cylinder axis of the front dispensing plunger 50 and extends into a recess of the limiting plunger 52. The guide element 60 prevents the front dispensing plunger 50 from tilting and thus from canting.

The cross-sectional view according to FIG. 7 shows how the locking element works and how it can be operated by means of the butterfly screw 20. The butterfly screw 20 has a shaft with two different diameters. The thinner shaft in the front can be pushed into a fitting thinner recess in the guide element 60 of the front dispensing plunger 50. The thinner shaft can be locked to the guide element 60 by means of a first bayonet closure 62. A second bayonet closure 64 is provided on the thicker shaft and can lock the thicker shaft to the limiting plunger 52. Thus, using the locking element made up of the two parts of the shaft, the bayonet closures 62, 64, and the butterfly screw 20, the front dispensing plunger 50 can be firmly connected to the limiting plunger 52.

The snap-in means 58 of the limiting plunger 52 are arranged on bendable fins and, when inserted, engage a circumferential groove on the inner walls of the first container 2, whereby the groove is arranged in the region of the rear of the first container 2. The limiting plunger 52 comprises gas passages (not shown) through which a gas can be evacuated from or supplied between the front dispensing plunger 50 and the limiting plunger 52.

By means of the fins and the snap-in means 58, the limiting plunger 52 can be detached manually from outside from the walls of the first container 2. For this purpose, the opposite snap-in means and/or the groove on the inner wall of the first container 2 is arranged so close to the rear end of the first container 2 that the rear part of the fins projects beyond the rear edge of the first container 2.

FIG. 8 shows a schematic side view of a device 1 according to the invention with a dosing plunger inserted. The screw cap 14 has been screwed fully onto the external thread. In the process, the contents of the opened second containers 4, 5 were fully transferred into the first container 2.

By rotating and pushing and pulling the dispensing tube 10 in and out, the mixing element connected to it is moved in the interior of the first container 2 and the content of the first container 2 is being mixed. After mixing, the dispensing tube 10 is pulled out of the internal space of the first container 2 to the stop (upwards in FIG. 7). During this process, the loose stoppers 22 become placed against intervening spaces of sufficient size between the mixing vanes 36 of the mixing facility 36. Subsequently, the core 30 in the interior of the dispensing tube 10 is pulled out of the dispensing tube 10 by means of the handle part 12 and the device 1 thus becomes opened towards the outside.

Propelling the dispensing plunger 18 or the front dispensing plunger 50 into the first container 2 dispenses the ready-mixed bone cement dough from the first container 2 via the dispensing tube 10 such that it can be applied.

The structure of the device 1 and its parts is in many parts symmetrical about a symmetry axis that is vertical with respect to the figures and/or with respect to a plane of symmetry, in which said symmetry axis is situated.

The features of the invention disclosed in the preceding description and in the claims, figures, and exemplary embodiments, can be essential for the implementation of the various embodiments of the invention both alone and in any combination.

LIST OF REFERENCE NUMBERS

1 Device/bone cement cartridge system
2 First container
4 First second container
5 Second second container
6, 24 Dosing plunger
8 Dosing funnel/filling aid
10 Dispensing tube
12 Handle part
14 Screw cap
16 External thread
18 Dispensing plunger
20 Butterfly screw
22 Lid/closure
26 Snap-in element
28 Opposite snap-in means
30 Core
32 Rod
34 Seal
36 Mixing vane/mixing facility
38 Fin
40 Ring
42 Internal thread
44, 45 Sealing ring
46 Guide sleeve
50 Front dispensing plunger
52 Limiting plunger
54 Spring
56 Wiper lip
58 Snap-in means/spring
60 Guide element/pin
62 Bayonet closure with guide element
64 Bayonet closure with limiting plunger

The invention claimed is:

1. A device for storing, mixing, and applying polymethylmethacrylate bone cement, the device comprising a first container for a first pasty component of the bone cement, a dispensing plunger is arranged such that it can be shifted in the first container and serves for extruding a content of the first container through a dispensing tube opposite from the dispensing plunger, wherein the dispensing tube is rotatable and shiftable in a longitudinal direction through a feed-through in a side of the first container opposite from the dispensing plunger, and a mixing facility, for mixing the content of the first container, is arranged in the first container and is secured to the dispensing tube such that the mixing facility is movable in the first container by moving the dispensing tube to mix the content of the first container, wherein at least one second container for at least one second component of the bone cement is arranged on the first container, wherein an internal space of the at least one second container is closed with respect to an internal space of the first container by means of a closure, which is openable, and wherein the at least one second container is limited, on a side opposite from the closure, by a dosing plunger and wherein at least one limiting surface of the first container is formed by a mobile volume compensation element.

2. The device according to claim 1, wherein the closure of the at least one second container is openable by exerting a pressure on the dosing plunger of at least one second container such that the first container is then connected to said at least one second container.

3. The device according to claim 1, wherein the mixing facility comprises at least two mixing vanes arranged on an end of the dispensing tube pointing into an inside of the first container and that extend radially from the dispensing tube outwards into the first container.

4. The device according to claim 3, wherein an axial height of the at least two mixing vanes is larger than a maximal outer diameter of the closure, wherein a hollow space between the at least two mixing vanes accommodates at least the closure.

5. The device according to claim 1, wherein the device comprises two second containers, that are limited on two opposite sides by one closure each and one dosing plunger each for dispensing a content of the second containers.

6. The device according to claim 1, wherein the closure is connected to a ring by means of a flexible fin, wherein the ring is arranged on an inside of the first container such as to be mobile about the dispensing tube such that a connection is axially mobile on the dispensing tube by means of the ring, or wherein the ring is secured to a guide sleeve that is arranged in the feed-through for the dispensing tube of the first container and guides the dispensing tube.

7. The device according to claim 1, further comprising an axially mobile core that is arranged in the dispensing tube and closes the dispensing tube on an end pointing into an inside of the first container, wherein, a circumferential sealing ring is arranged on the axially mobile core and seals the axially mobile core with respect to an inner wall of the dispensing tube.

8. The device according to claim 1, wherein the dispensing plunger is lockable with respect to the first container on an end of the first container opposite from the dispensing tube.

9. The device according to claim 1, wherein the mobile volume compensation element is implemented by means of the dispensing plunger, wherein the dispensing plunger is designed to be made of two parts comprising a front dispensing plunger in the front of the dispensing plunger and a limiting plunger, that are supported in the first container such as to be mobile with respect to each other, the front dispensing plunger and the limiting plunger, and the motion of the front dispensing plunger out of the first container is limited by the limiting plunger, wherein the limiting plunger is lockable in the first container, wherein the limiting plunger comprises a snap-in mechanism that is detachable from outside and engages an opposite snap-in mechanism on the first container.

10. The device according to claim 9, wherein a gas passage opening is provided in at least one of the limiting plunger and between the limiting plunger and the first container, wherein the gas passage opening is or are suitable for discharging a gas from and filling a gas in between the front dispensing plunger and the limiting plunger.

11. The device according to claim 9, wherein a guide element is arranged on the front dispensing plunger that is guided in a matching opening in the limiting plunger, wherein the guide element is a cylindrical pin that extends into a matching cylindrical feed-through in the limiting plunger.

12. The device according to claim 9, wherein a detachable locking element blocks an axial motion of the front dispensing plunger with respect to the limiting plunger while the device is in a storage condition.

13. The device according to claim 1, wherein the mobile volume compensation element or at least one additional volume compensation element is supported through an elastic spring such as to be mobile with respect to the first container, wherein the spring is configured to push the volume compensation element in a direction of the internal space of the first container.

14. The device according to claim 1, wherein at least one porous gas-permeable sealing ring is arranged on an external surface of the at least one dosing plunger such that a gas exchange between a space formed by an inner walls of the at least one second container, the closure, and the dosing plunger, and a surrounding atmosphere can take place.

15. The device according to claim 1, wherein the at least one dosing plunger possesses at least one directional snap-in element that can engage at least one opposite snap-in mechanism on the inner surface of the at least one second container in manner such that, after snapping-in takes place, a backward motion of the dosing plunger out of the at least one second container cannot take place.

16. The device according to claim 1, wherein the at least one second container for the at least one second component of the bone cement is arranged on the first container on the same side as the feed-through for the dispensing tube and adjacent to the feed-through for the dispensing tube.

17. A method for producing a polymethylmethacrylate bone cement using the device according to claim 1, the method comprising:
  A) providing the device, wherein the first container is filled with a first liquid or pasty component of the PMMA bone cement and the at least one second container is filled with a second component of the PMMA bone cement;
  B) opening the at least one second container by pushing the dosing plunger forward and dispensing the second component from the at least one second container into the first container by further propelling the dosing plunger forward, wherein the change of volume of the content of the first container upon the introduction of the second component into the first container is compensated for through a motion of the mobile volume compensation element and
  C) mixing the components in the first container through moving the mixing facility, wherein moving the mixing facility is associated with the dispensing tube connected to the mixing facility being pushed into and pulled out of the first container repeatedly, wherein the change of volume of the content of the first container during mixing is compensated for through a motion of the mobile volume compensation element.

18. The method according to claim 17, wherein a core is removed from the dispensing tube after C), and the method further comprises: D) applying the mixed bone cement by driving the dispensing plunger forward in the first container through the dispensing tube.

19. The method according to claim 17, wherein the content of the first container is mixed by moving the mixing facility, which is connected to the dispensing tube, in the first container by moving the dispensing tube into and out of the first container, wherein, in addition, the mixing facility is rotatable in the first container by rotating the dispensing tube.

20. The method according to claim 17, wherein the interior of the first container and the interior of the at least one second container are de-gassed and sterilised before A)

occurs, wherein a limiting plunger, a front dispensing plunger and/or a volume compensation element are lockable, and subsequently the first container is filled with a first component of the bone cement and the at least one second container is filled with a second component of the bone cement, wherein, concurrently or subsequently, an antibiotic or a mixture of antibiotics are filled into at least one second container.

21. The method according to claim 17, wherein the dispensing tube, after mixing, is moved out in the direction out of the first container such that the mixing facility touches against a front inner surface of the first container.

22. The method according to claim 17, wherein the dosing plunger, after being pushed in completely, is affixed irreversibly against the at least one second container by means of a snap-in mechanism.

* * * * *